(12) United States Patent
Runkel et al.

(10) Patent No.: US 7,943,184 B2
(45) Date of Patent: May 17, 2011

(54) PROCESS FOR PREPARING AN EXTRACT FROM IVY LEAVES

(75) Inventors: Frank Runkel, Buseck (DE); Wolfgang Schneider, Butzbach (DE); Oliver Schmidt, Buseck (DE); Georg Maximilian Engelhard, Kronberg (DE)

(73) Assignee: Engelhard Arzneimittel GmbH & Co. KG, Niederdorfelden (DE)

( * ) Notice: Subject to any disclaimer, the term of this patent is extended or adjusted under 35 U.S.C. 154(b) by 0 days.

(21) Appl. No.: 11/384,944

(22) Filed: Mar. 17, 2006

(65) Prior Publication Data
US 2006/0210660 A1 Sep. 21, 2006

Related U.S. Application Data

(63) Continuation of application No. PCT/EP2004/010092, filed on Sep. 10, 2004.

(30) Foreign Application Priority Data

Sep. 19, 2003 (DE) .................... 103 45 343

(51) Int. Cl.
| | |
|---|---|
| *A61K 36/25* | (2006.01) |
| *A61K 31/704* | (2006.01) |
| *A61K 127/00* | (2006.01) |
| *A61P 11/00* | (2006.01) |
| *C12P 19/56* | (2006.01) |
| *C12S 3/00* | (2006.01) |

(52) U.S. Cl. ............ 424/774; 424/725; 514/33; 435/78; 435/267

(58) Field of Classification Search ........................ None
See application file for complete search history.

(56) References Cited

FOREIGN PATENT DOCUMENTS

| DE | 30 25 223 | | 1/1981 |
|---|---|---|---|
| DE | 101 12 168 A1 | | 10/2002 |
| GB | 2 051 575 | | 1/1981 |
| GB | 2051575 A | * | 1/1981 |

OTHER PUBLICATIONS

Crespin et al., Chromatographia (1994), vol. 38, No. 4/4, pp. 183-186.*
Remington's Pharmaceutical Sciences (17$^{th}$ Ed. 1985), pp. 99,. 1417.*
STN online, file EMBASE, Acc. No. 96268188, (Gladovic et al., Farmacevtski Vestnik (1996), vol. 47, No. 2, pp. 239-245), Abstract.*
STN online, file CAPLUS, Acc. No. 1991:520159, (Elias et al., Journal de Pharmacie de Belgique (1991), vol. 46, No. 3, pp. 177-181), Abstract.*
STN online, file CAPLUS, Acc. No. 1990:52212, (Hahn et al., Chemical & Pharmacetuical Bulletin (1989), vol. 37, No. 8, pp. 2234-2235), Abstract.*

(Continued)

*Primary Examiner* — Ernst V Arnold
*Assistant Examiner* — Christopher R Lea
(74) *Attorney, Agent, or Firm* — Harness, Dickey & Pierce, P.L.C.

(57) ABSTRACT

The present invention relates to a process for preparing an extract from ivy leaves which includes the active ingredient hederacoside C and α-hederin, and to extracts prepared by this process. According to this there is initially provision of a first, α-hederin-rich extract and subsequently provision of a second, hederacoside C-rich extract. In a last step, the two extracts are blended to give an extract which has an adjusted hederacoside C content and an adjusted α-hederin content.

10 Claims, 1 Drawing Sheet

OTHER PUBLICATIONS

Remington's Pharmaceutical Sciences (17th Ed. 1985), pp. 1516,1517.*

Joy et al., Medicinal Plants (1998), pp. 23-26.*

Schlösser, E "Role of Saponins in antifungal resistance 11: The hederasponins in leaves of English ivy (Hedera helix)", Zeitschrift für Pflanzenkrankheiten and Pflanzenschutz (Journal of Plant Diseases and Protection), 1973, vol. 80, pp. 704-710.*

XP009041755—Andreas Trute et al.; "In Vitro Antispasmodic Compounds of the Dry Extract Obtained from Hedera helix"; 1997; pp. 125-129.

XP1001204524—Von Hildebert Wagner et al.; "Extracts of Hedera helix leaves: HPLC analysis"; 1986; pp. 2613-2617.

G. Wulff; "Neuere Entwicklungen auf dem Saponingebiet"; 1986; pp. 797-808.

* cited by examiner

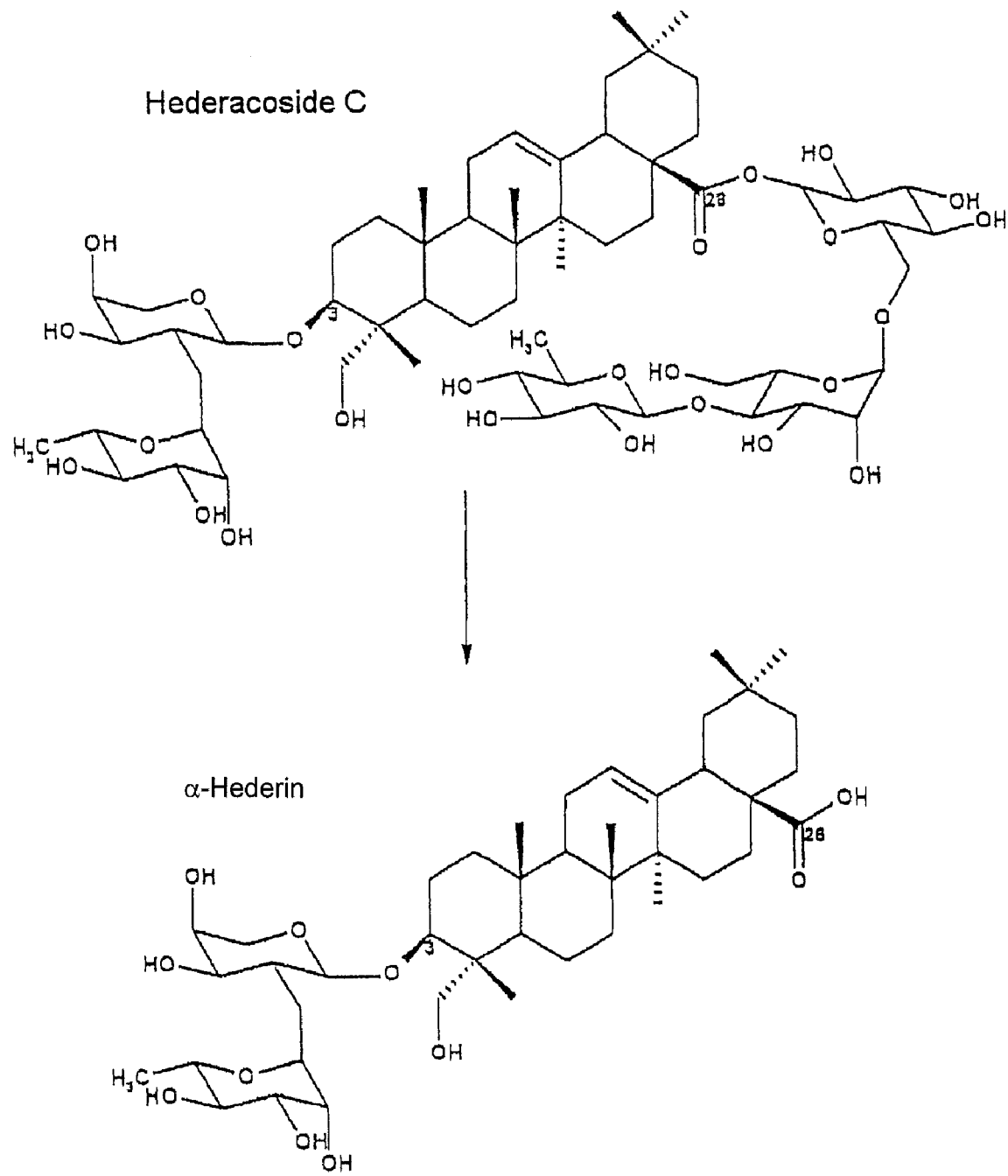

US 7,943,184 B2

PROCESS FOR PREPARING AN EXTRACT FROM IVY LEAVES

CROSSREFERENCE OF PENDING APPLICATIONS

This application is a continuation of pending international application PCT/EP2004/010092 filed on Sep. 10, 2004 which designates US and which claims priority of German patent application No. 103 45 343.1 filed on Sep. 19, 2003

BACKGROUND OF THE INVENTION

The present invention relates to a process for preparing an extract from ivy leaves.

Extracts from ivy leaves are currently employed successfully in particular for the therapy of respiratory disorders because the extract shows spasmolytic, expectorant and antiobstructive effects. These effects are attributable in particular to the therapeutically important constituents of the ivy leaf extracts, which belong to the class of triterpene saponins.

The chief saponin in this connection is the bisdesmosidic hederacoside C and the α-hederin which is produced therefrom by ester hydrolysis. A further saponin which has been detected is hederagenin.

Since extracts from ivy leaves can be obtained by various processes, these extracts often display different potencies. This derives from the fact that the content of the constituents depends not only on the natural composition but also on the particular method for preparing the extract.

It has been possible to show in recent studies by the applicant that α-hederin is the really active substance in ivy leaves and contributes to the bronchospasmolysis because this substance causes relaxation of smooth muscles via binding to β-adrenergic receptors and cascades induced thereby.

Extracts from plant materials—especially dry extracts— and processes for preparing such extracts are described many times in the area of pharmacy and pharmaceutical preparations.

One process for preparing dry extracts from plant materials is disclosed for example in DE 101 12 168 A1. It is said that the content of lipophilic and hydrophilic substances can be adjusted using the process disclosed therein. In this case, the plant material is subjected to at least two extractions with solvents of different lipophilicity, and the extracts are obtained therefrom separately. The extracts are dried separately from one another and mixed in the desired ratio. It is possible in this way to adjust the content of lipophilic and hydrophilic substances. The process is said also to be suitable for obtaining dry extracts from ivy (*Hedera helix*).

However, this publication discloses neither an extract which has a specifically adjusted content of α-hederin and/or hederacoside C, nor a process with which such an extract could be provided.

Furthermore, DE 30 25 223 A1 discloses a pharmaceutical preparation based on ivy extracts and a process for the preparation thereof, where the preparations rations include as active ingredient a 90% or 60% hedera saponin C-containing extract or α-hederin. The extract is obtained by using acetone and methanol. In order to convert hedera saponin C or hederacoside C into α-hederin, in order thus to obtain an extract with only α-hederin, in the said application the 90% extract is hydrolysed with sodium hydroxide or potassium hydroxide.

A process with which it is possible to prepare an extract in which α-hederin and hederacoside C are present in a content which can be adjusted as desired is, however, not disclosed in this publication either.

However, in order to ensure a reproducible therapeutic effect, it is precisely desirable to have ivy extracts which have a definable content of active ingredients.

A further disadvantage of extracts employed to date is that these extracts have to be administered more than once in order to have an immediate and lasting bronchospasmolytic effect inducible by α-hederin. The reason for this may be that the bioavailability of α-hederin is insufficient because, for example, the α-hederin content present in the extract is too low at the start of intake. On the other hand, α-hederin originally present in the extract is also absorbed relatively quickly in vivo, making multiple administrations necessary in order to achieve a therapeutic effect.

Taking account of the above statements, it is therefore an object of the present invention to provide a process for preparing an extract, and an extract by which a rapid bioavailability of α-hederin and maintenance of the bioavailability over a prolonged period is ensured.

SUMMARY OF THE INVENTION

The object on which the invention is based is achieved by preparing an extract from ivy leaves having an adjustable content of hederacoside C and α-hederin, where the process includes the following steps:

a) providing a first, α-hederin-rich extract, having at least 3% α-hederin;

b) providing a second, hederacoside C-rich extract, having at least 5% hederacoside C; and c) blending the first and the second extract to give an extract which has an adjusted hederacoside C content and an adjusted α-hederin content.

It is possible with the process of the invention to obtain an extract which on the one hand has α-hederin available as immediately acting substance, and on the other hand also hederacoside C, which is converted into α-hederin in vivo. Moreover the first extract includes α-hederin and the second extract includes hederacoside C, in each case in highly enriched form.

The first extract can in this connection be prepared for example by the starting material, for example the dried herb, firstly being comminuted and subjected to a fermentation step, and thereafter being preswollen and extracted for example in an alcohol/water mixture, for example 30% ethanol. Finally, it is possible for example for a thin-film vaporization and a spray drying to take place. Depending on the desired α-hederin content, the whole herb can be fermented—in this way all the hederacoside C present in the starting plant material is converted into α-hederin. On the other hand, it is also possible for only part of the starting plant material to be fermented, and the remaining parts to be admixed only for the preswelling in ethanol—α-hederin only is present greatly enriched thereby.

"Fermentation" means herein the breakdown or the conversion of constituents present in an original substance into other substances by addition of a fermentation medium, for example water, to the original substance, with particular parameters, for example time and temperature, being adjusted where appropriate to the fermentation process. This novel fermentation step opens up the possibility of specifically preparing α-hederin-rich extracts.

The ivy leaves can in this connection be employed for example as dried herb. Dried herbs have the advantage in the preparation of pharmaceuticals that they are in some circumstances easier to handle in terms of stability than are fresh herbs. Nevertheless, the use of fresh ivy leaves is not precluded for the extract of the invention.

Dried medicinal plants and parts of medicinal plants are referred to as "herbs" by definition in the area of pharmaceutical technology. The use of such medicinal plants in the form of "herbs" can moreover take place either in unaltered or in comminuted form.

The second extract can be prepared for example by the dried herb being mixed immediately after cutting with an extractant, for example 30% ethanol, and being extracted by conventional methods. Alternatively, the comminuted herb can—before the ethanol extraction—be steamed with superheated steam. Experiments by the inventors have shown that it was possible via this treatment for the content of hederacoside C in the extract to be increased, or stabilized in relation to the initial content, and the α-hederin content to be reduced. In these ways, extracts which can be employed as second, hederacoside C-rich extract in step b) of the process of the invention are obtained. This novel steaming step opens up the possibility of specifically preparing hederacoside C-rich extracts.

It is moreover particularly preferred in the process if the α-hederin-rich extract in step a) has an α-hederin content of at least 5%.

It is further preferred for the hederacoside C-rich extract in step b) to have a hederacoside C content of at least 10% and an α-hederin content of less than 2%.

It is moreover preferred if in the process the extract to be obtained in step c) has a hederacoside C content of about 6.5%, and an α-hederin content of about 4.0%.

The object on which the invention is based is further achieved by an extract which is prepared by the process of the invention. In particular, the object on which the invention is based is achieved by an extract, prepared by the process of the invention, from ivy leaves having an adjusted hederacoside C content of at least 5%, in particular of about 6.5%, and an adjusted α-hederin content of at least 3%.

This is because the extract of the invention has the advantage, owing to the adjusted content of the said active ingredients, that after a use of the extract the active ingredient α-hederin is initially made available rapidly through the α-hederin which is present as such in the extract. The hederacoside C which is present in the extract in addition to α-hederin is moreover absorbed in vivo with a time lag, and is gradually converted into α-hederin, so that after the originally present α-hederin has been used up, the α-hederin converted from hederacoside C is available. This ensures in an advantageous manner that the therapeutic efficacy of the extract, or of the medicament including the extract, is longer.

The inventors have demonstrated this process in their own experiments. In this connection, they showed that it was possible with an extract of the invention, in which the α-hederin and hederacoside C active ingredient content was adjusted in the abovementioned optimal range, to achieve a rapid rise in level and maintenance of a constant concentration. A comparative extract having a higher hederacoside C content and a lower α-hederin content had to be administered more frequently than the extract of the invention in order to achieve comparable concentration levels. Accordingly, it is possible with the novel extract to attain even by a single administration an α-hederin concentration which is desirable for use for bronchospasmolysis.

It is especially preferred in this connection for the extract to be prepared by the process of the invention, and to have a hederacoside C content of about 6.5% and an α-hederin content of about 4.0%.

The invention further relates to the use of the extract of the invention for preparing a medicament, in particular for the treatment of respiratory disorders, and to a medicament which includes the extract of the invention.

The extracts of the invention with an adjusted content of the hederacoside C and α-hederin constituents are particularly advantageous in the use as medicaments because reproducible therapeutic effects can be achieved with them and, in addition, an immediate provision of the active ingredient α-hederin with spasmolytic activity is made possible, and the provision is maintained constant over a prolonged period.

The medicament of the invention can accordingly be employed for the treatment of respiratory disorders such as, for example, infectious inflammatory respiratory disorders such as, for example, pneumonia, tracheitis, bronchitis etc., but also for obstructive and restrictive pulmonary disorders such as chronic bronchitis, bronchial asthma, bronchiectases etc., i.e. for respiratory disorders in which relaxation of smooth muscles is desired.

The medicament may be in the form of capsules, tablets, coated tablets, suppositories, granules, powders, solutions, creams, emulsions, aerosols, ointments and oils. Oral administration forms are particularly preferred in this connection. The medicament may moreover include excipients which are conventionally used in preparing medicaments. A number of suitable substances is to be found for example in A. Kibbe, Handbook of Pharmaceutical Excipients, 3rd ed. 2000, American Pharmaceutical Association and Pharmaceutical Press.

BRIEF DESCRIPTION OF THE DRAWINGS

Further advantages are evident from the example and the appended figure, which shows:

The hydrolysis of hederacoside C to α-hederin.

It will be appreciated that the features which are mentioned above and are to be explained hereinafter can be used not only in the particular combination indicated but also in other combinations or alone, without leaving the scope of the present invention.

DETAILED DESCRIPTION OF PREFERRED EMBODIMENTS

EXAMPLE

1. Absorption Characteristics of Ivy Leaf Constituents in vivo (Rats)

It was possible to show in an absorption study by means of the biopharmaceutics classification system (BCS) that α-hederin is to be attributed with a moderate absorption (10-90%). Under the same conditions, hederacoside C did not permeate through the membranes, for which reason a possible absorption of hederacoside C in the form of α-hederin was to be investigated. Absorption studies were carried out on rats for this purpose.

The influence of administration of two different extracts on the plasma concentration of α-hederin was subsequently investigated. The change in the plasma concentration of α-hederin with a single administration compared with multiple administration of the extract and with different blood sampling times after administration was also investigated, as was the α-hederin absorption rate. Two extracts whose saponin distribution is shown in Table 1 below were selected for this purpose:

All percentages given are % by weight.

TABLE 1

Saponin distribution of the extracts

|  | Hederacoside C content [%] | α-Hederin content [%] |
|---|---|---|
| Extract A | 14.5 | 0.9 |
| Extract B | 6.5 | 4.0 |

For intravenous administration, the required amount of extract was dissolved in 11% (m/m) ethanol, filtered and injected. It was aimed to administer a volume of 2 ml of extract solution (dose in each case [mg/kg of bodyweight]: 25). A blood sample was taken from the animals 5 minutes after the administration. About 2 ml of whole blood with added EDTA for anticoagulation were required for each sample.

Suspensions of the extracts in glycerol were prepared for oral administration. The animals were gavaged with about 2 ml of these suspensions (dose in each case [mg/kg of bodyweight]: 1000 and 166.66). 2 ml of blood were taken from each of the animals 1 and 3 hours after the last administration in each case. The animals had an average weight of about 200 g and a blood volume of about 20 ml.

The results of the analyses are shown in Table 2 below:

TABLE 2

Summary of administration/α-hederin plasma concentration

| Type of sample | Administration | Admin. extract | Dose admin. [mg/kg] | Blood sampling time | α-Hederin plasma concentration in [µg/ml] |
|---|---|---|---|---|---|
| Blank sample | none | — | — | — | 0.0 |
| Reference | i.v. | A | 25 | 5 min after admin. | 2.3 |
| Sample | p.o. single admin. | A | 1000 | 1 h after admin. | 3.3 |
| Sample | p.o. single admin. | A | 1000 | 3 h after admin. | 6.3 |
| Sample | p.o. 3 days 2x a day | A | 166.66 | 1 h after last admin. | 20.8 |
| Reference | i.v. | B | 25 | 5 min after admin. | 10.0 |
| Sample | p.o. single admin. | B | 1000 | 1 h after admin. | 11.1 |
| Sample | p.o. single admin. | B | 1000 | 3 h after admin. | 14.4 |
| Sample | p.o. 3 days 2x a day | B | 166.66 | 1 h after last admin. | 14.9 |

Hederacoside C was not detectable in any sample. As can be inferred from Table 2 above, the measured α-hederin plasma concentration on multiple administration of an extract of lower α-hederin content is higher than on comparable administration of an extract richer in α-hederin. This result was explicable by a recalculation which is shown in Table 3 below:

TABLE 3

Absorption rates for administration of extract A (14.5% hederacoside C and 0.9% α-hederin)

| Mode of administration/ blood sampling | α-Hederin plasma conc. [µg/ml] | Max. attainable conc. (theoretical) | Absorption rate [%] | Max. attainable blood levels considering the total saponin content [µg/ml] | Absorption rate [%] |
|---|---|---|---|---|---|
| Single admin./ 1 h after admin. | 3.3 | 90 | 3.7 | 980 | 0.33 |
| Single admin./ 3 h after admin. | 6.3 | 90 | 7.0 | 980 | 0.64 |
| Multiple admin./ 1 h after admin. | 20.8 | 90 | 23.1 | 980 | 2.12 |

The total saponin content takes account of the molar masses of the two constituents and is based on α-hederin. The total saponin content in extract A in this case was 9.8%, based on α-hederin. A blood volume of 20 ml was assumed.

The calculations for extract B are shown in Table 4 below:

TABLE 4

Absorption rates for administration of extract B (6.5% hederacoside C and 4.0% α-hederin)

| Mode of administration/ blood sampling | α-Hederin plasma conc. [μg/ml] | Max. attainable conc. (theoretical) | Absorption rate [%] | Max. attainable blood levels considering the total saponin content [μg/ml] | Absorption rate [%] |
|---|---|---|---|---|---|
| Single admin./ 1 h after admin. | 11.1 | 400 | 2.8 | 800 | 1.38 |
| Single admin./ 3 h after admin. | 14.4 | 400 | 3.6 | 800 | 1.80 |
| Multiple admin./ 1 h after admin. | 14.9 | 400 | 3.7 | 800 | 1.86 |

The total saponin content takes account of the molar masses of the two constituents and is based on α-hederin. The total saponin content in extract B in this case was 9.8%, based on α-hederin. A blood volume of 20 ml was assumed.

In summary, it can be said that multiple administration of an α-hederin-rich and of an α-hederin-poor extract led to comparable a-hederin plasma concentrations. However, if the hederacoside C content of the two extracts is taken into account, and the total content of the two saponins is determined, calculated as α-hederin, the two extracts differ only slightly. It must be concluded on the basis of these results that elimination of the sugar located at C28 of hederacoside C takes place in vivo and results in absorbable α-hederin. This process - i.e. conversion of hederacoside C into α-hederin - is shown in the appended figure.

It can be concluded from the in vitro demonstration of a spasmolytic activity of α-hederin in contrast to hederacoside C and the recovery of α-hederin in the plasma in contrast to hederacoside C that the α-hederin concentration in the blood correlates decisively with the therapeutic effect demonstrated in many clinical studies.

Using an extract which is optimized in relation to the therapeutic effect ought therefore to result rapidly in a uniform plasma concentration, which is also maintained on multiple administration of the extract. Extract B represents such an extract, and administration thereof—in contrast to extract A—leads after only one hour to a plasma concentration which is comparable with the plasma concentration after multiple administration. Extract B with a content of 6.5% hederacoside C and 4.0% α-hederin was notable for a rapid onset of action and for reproducibility of the therapeutic effect.

The range of content of hederacoside C and α-hederin in an extract which is optimal for the therapeutic effect can therefore be stated on the basis of extract B as follows:
Hederacoside C: 5-8%
α-Hederin: 3-5%

2. Preparation of an Optimized Ivy Extract

The optimized ivy extract is notable for a range of contents which is batch-consistent within certain limits—based on the constituents hederacoside C and α-hederin. The specified content of hederacoside C should in this connection be 50 to 80 mg/g, and that of α-hederin should be 30 to 50 mg/g. A plurality of extracts were mixed in order to comply with these specifications. The extracts, which were obtained by conventional processes, are, however, only conditionally suitable for such mixing processes because their content of the relevant active ingredient is often insufficiently high.

Extraction processes leading to ivy leaf extracts which are notable in each case for a high content of one of the two hedera saponins, while the respective other hedera saponin is at the same time present only in very small amounts, are described below.

a) Preparation of an α-hederin-rich Extract

The basis for controlling the ratio of hederacoside C to α-hederin in this extraction process is specific inclusion of elimination of the sugar located at C28 of hederacoside C in the extraction process. Since conversion of hederacoside C into α-hederin proceeds almost quantitatively, virtually any batch of leaves is suitable as starting material for preparing an α-hederin-rich extract.

After quality testing and release by the quality control department, part of the herb (ivy leaves DAC) was highly comminuted in a mill, a maximum size of the fragments of 2×2 mm being guaranteed by a protective screen. In addition, the screened material was checked visually for larger particles and contaminants.

The aqueous portion of 6 parts of extractant (30% (m/m) ethanol) was added to the comminuted sample. This mixture was fermented at 30° C. with occasional mixing/agitation for 60 min.

The 96% ethanol portion of 6 parts of extractant was then added, and the mixture was homogenized by stirring.

After a 6-hour preswelling phase, the eluate was removed and the remaining herb was percolated with the remaining 6 parts of the extractant.

The combined eluates were filtered once again to exclude small herb particles and were homogenized before they were dried by thin-film vaporization at 55° C. and 150 mbar to give the concentrate. This was homogenized and then dried by spray drying at 45 to 60° C. to give the ivy leaf dry extract.

To check this preparation process, the following extracts were prepared: starting from ivy leaves with a content of 3.91% hederacoside C and 0.20% α-hederin, an extract was produced once by the conventional method (comminution of the dried sample with addition immediately thereafter of 30% (m/m) ethanol and extraction) and once by the novel method. Table 5 below shows the chromatographic results for the content of α-hederin and hederacoside C:

TABLE 5

Content of α-hederin and hederacoside C in the extracts

|  | α-Hederin (%) | Hederacoside C (%) | Total saponins calculated as hederacoside C |
|---|---|---|---|
| Conventional | 0.53 | 8.68 | 9.54 |
| Novel | 4.74 | 0 | 7.71 |

As is evident from the table, it was possible with the novel extraction process to convert the hederacoside C present in the leaves completely into α-hederin.

Since the total saponin content, calculated as hederacoside C, is also of the same order of magnitude, it is possible—with knowledge of the appropriate saponin concentration in the herb and taking account of the enrichment factor of about 2 to 3—to estimate the final α-hederin content in the extract.

In order to convert only part of the hederacoside C present in the herb into α-hederin, it is accordingly possible to subject only a certain portion of the herb to the fermentation with water, with all the other parameters remaining constant. After the 60-minute fermentation is complete, the remaining herb and the ethanol is then added for the 6-hour preswelling. The final α-hederin content in the extract can be estimated with knowledge of the appropriate saponin concentration in the herb and taking account of the enrichment factor of about 2-3.

It is accordingly possible with the process of the invention to alter markedly the range of constituents of an ivy leaf dry extract by introducing a fermentation without a great expenditure of time and resources. Not the least of the effects is the benefit for the efficacy of the extract through the specific influence on the α-hederin content in a dry extract, or medicament, owing to the numerous publications on the efficacy of α-hederin.

b. Preparation of Ivy Leaf Dry Extracts With Increased Hederacoside C Content

The basis for controlling the ratio of hederacoside C to α-hederin is specifically to suppress the elimination of the sugar located at C28 of hederacoside C during the extraction process. Care should be taken in the selection of the batch of herbs that leaf batches with a low α-hederin content are employed. A specification of less than 0.5% of α-hederin based on the dried herb is advisable.

A homogeneous sample of ivy leaves was analysed for the content of the two saponins as follows:
Hederacoside C: 6.37%
α-Hederin: 0.85%

In each case three extractions were carried out starting from the herb by the following extraction method:
3 g of the dried herb which had been comminuted to about 3×3 mm were steamed with superheated steam of about 120° C. for a few seconds. The herb treated in this way was preswollen with 18 g of the extractant (30% (m/m) ethanol) for about 6 hours. After the miscella had been drained off, the remaining herb was percolated with a further 18 g of the extractant. This miscella was dried in a vacuum drying oven. Alternatively, the drying can take place for example by thin-film vaporization at, for example, 55° C. and 150 mbar and subsequent spray drying at 45-60° C.

The extraction temperature is preferably between about 20 and about 40° C., in particular at about 30° C. The ratio of herb to extractant is in this case for example 1:12.

After analysis of the resulting extracts it was possible to record the results detailed in Table 6 below:

TABLE 6

Content of hederacoside C and α-hederin in the steamed extracts

| Sample | Hederacoside C content [%] | α-hederin content [%] | Content of hederasaponins calculated as hederacoside C [%] |
|---|---|---|---|
| Initial herb | 6.37 | 0.85 | 7.75 |
| Extract steamed 1 | 14.33 | 0.85 | 15.71 |
| Extract steamed 2 | 14.26 | 0.85 | 15.64 |
| Extract steamed 3 | 14.57 | 0.71 | 15.72 |

Leaf dry extracts prepared by this method accordingly had the α-hederin amount maximally present in the leaves employed. Thus, overall, storage-stable extracts with a high hederacoside C content and very low α-hederin content were obtained. On use of batches of leaves with a content of less than 0.5% α-hederin, it is also possible to assume a maximum α-hederin content of 0.5% for the resulting extract.

c. Mixing the Two Enriched Extracts

It is possible by means of the extraction processes described under 2a) and 2b) to prepare ivy leaf extracts each of which contain one of the two hedera saponins in enriched form.

Finally, the two enriched extracts are used to prepare a mixture for the final special extract with a content of 5-8% hederacoside C and 3-5% α-hederin.

EXAMPLE 1 part of extract A with about 7.5% α-hederin+1 part of extract B with about 13.0% hederacoside C and 0.5% α-hederin→Extract with 6.5% hederacoside C and 4.0% α-hederin.

This calculation must of course be adjusted each time for the levels of content of the two enriched extracts, but adjustment of the two enriched extracts to the concentrations mentioned in the example by mixing different enriched extracts is also conceivable.

It is now possible to formulate a medicament which ensures, even with a single administration, that the actual active ingredient (α-hederin) is rapidly available in the body. The simultaneously high hederacoside C content means that a high α-hederin level can be maintained for a long time because the hederacoside C is continuously converted into α-hederin in the body.

This means that the medicament need not be taken more than once, which increases patient compliance. Respiratory disorders which frequently occur in children are one area of use of ivy extracts. Since children are often reluctant to take medicaments, successful treatment is now possible with fewer administrations.

Therefore, what is claimed, is:
1. A process for preparing an extract from ivy leaves having as active ingredients hederacoside C and α-hederin, with the steps of:
 a) providing a first, α-hederin-rich extract, by treating ivy leaves to convert the hederacoside C contained in said ivy leaves into α-hederin, followed by an extraction to obtain an αhederin extract having at least 3% by weight α- hederin;

b) providing a second, hederacoside C-rich storage-stable extract, having at least 5% by weight hederacoside C, by treating comminuted ivy leaves with superheated steam, followed by an extraction resulting in said second, hederacoside C-rich storage-stable extract; and c) blending said first and said second extract to give an extract which has an adjusted hederacoside C content and an adjusted α-hederin content.

2. The process of claim 1, wherein said α-hederin-rich extract has an α-hederin content of at least 5% by weight.

3. The process of claim 1, wherein said hederacoside C-rich extract has a hederacoside C content of at least 10% by weight and an α-hederin content of less than 2% by weight.

4. The process of claim 1, wherein said extract to be obtained in step c) has an adjusted hederacoside C content of about 6.5% by weight and an adjusted α-hederin content of about 4% by weight.

5. The process of claim 1, wherein said second, hederacoside C-rich extract is produced by blocking an enzyme in ivy leaves which acts in the conversion of hederacoside C into α-hederin by treating said ivy leaves with superheated steam, followed by an extraction.

6. A method of making a therapeutic composition comprising:
   fermenting ivy leaves to create an α-hederin rich extract;
   steam super heating comminuted ivy leaves followed by an extraction to create a storage-stable hederacoside C-rich extract; and
   blending said α-hederin rich extract and said storage-stable hederacoside C-rich extract to create a therapeutic composition comprising about at least 3% by weight of α-hederin and at least 5% by weight of hederacoside C.

7. The method according to claim 6, wherein said α-hederin rich extract has an α-hederin content of at least 5% by weight.

8. The method according to claim 6, wherein said hederacoside C rich extract has a hederacoside C content of at least 10% by weight and an α-hederin content of less than 2% by weight.

9. The method according to claim 6, wherein said therapeutic composition comprises 3% to 5% by weight α-hederin and 5% to 8% by weight hederacoside C.

10. The method according to claim 6, wherein said therapeutic composition comprises about 4% by weight α-hederin and about 6.5% by weight hederacoside C.

* * * * *

UNITED STATES PATENT AND TRADEMARK OFFICE
CERTIFICATE OF CORRECTION

| | | |
|---|---|---|
| PATENT NO. | : 7,943,184 B2 | Page 1 of 1 |
| APPLICATION NO. | : 11/384944 | |
| DATED | : May 17, 2011 | |
| INVENTOR(S) | : Runkel et al. | |

It is certified that error appears in the above-identified patent and that said Letters Patent is hereby corrected as shown below:

<u>Title Page</u>, (56) References Cited, OTHER PUBLICATIONS,
line 5, after "96268188," insert -- Doc. No. 1996268188 --.
line 7, after "1991:520159," insert -- Doc. No. 115:120159 --.
line 10, after "1990:52212," insert -- Doc. No. 112:52212 --.

<u>Column 10</u>,
line 66, "αhederin" should be -- α-hederin --.

<u>Column 11</u>,
Line 9, "αhederin" should be -- α-hederin --.

<u>Column 12</u>,
Lines 7 and 12, "αhederin" should be -- α-hederin --.

Signed and Sealed this
Twelfth Day of July, 2011

David J. Kappos
*Director of the United States Patent and Trademark Office*